(12) United States Patent
Huang et al.

(10) Patent No.: US 10,775,303 B2
(45) Date of Patent: Sep. 15, 2020

(54) BIOLOGICAL SIGNAL ANALYZING DEVICE, BIOLOGICAL SENSING APPARATUS, SENSING METHOD AND FABRICATION METHOD OF BIOLOGICAL SIGNAL ANALYZING DEVICE

(71) Applicant: NATIONAL CHIAO TUNG UNIVERSITY, Hsinchu (TW)

(72) Inventors: Cheng-Sheng Huang, Hsinchu (TW); Chan-Te Hsiung, Taichung (TW); Yen-Chieh Wang, Changhua (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 16/440,454

(22) Filed: Jun. 13, 2019

(65) Prior Publication Data
US 2020/0182785 A1    Jun. 11, 2020

(30) Foreign Application Priority Data
Dec. 11, 2018 (TW) .............................. 107144604 A

(51) Int. Cl.
*G01N 21/41* (2006.01)
*G01N 33/483* (2006.01)

(52) U.S. Cl.
CPC ........... *G01N 21/41* (2013.01); *G01N 33/483* (2013.01)

(58) Field of Classification Search
CPC .......................... G01N 21/658; G01N 21/554
See application file for complete search history.

(56) References Cited

U.S. PATENT DOCUMENTS 3,814,498 A * 6/1974 Tomlinson, III ... G02B 27/4244
385/37
3,980,883 A * 9/1976 Franks ..................... G21K 1/06
378/84
(Continued)

FOREIGN PATENT DOCUMENTS

TW           201305549 A1      2/2013

OTHER PUBLICATIONS

Lin et al., "Linear Variable Filter based an a Gradient Grating Period Guided-Mode Resonance Filter," IEEE Photonics Technology Letters, 2015, pp. 1-4.

*Primary Examiner* — Kara E. Geisel
(74) *Attorney, Agent, or Firm* — Birch, Stewart, Kolasch & Birch, LLP

(57) ABSTRACT

A biological signal analyzing device configured to generate a first detection image or a second detection image is provided. The biological signal analyzing device includes a light-incident surface, a light-emitting surface and a plurality of optical-resonance structures. The sample is placed near the light incident surface, and receives a first light through the sample. The light resonance structures are configured to process the first light and generate a second and third light. The second light emits from the light emitting surface, and adapted to form the first detection image corresponding to the sample, and the third light emits from the light incident surface, and adapted to form the second detection image corresponding to the sample. The optical resonance structures vary their thickness along the first direction or vary the width along the second direction. A biological sensing apparatus, a sensing method and a fabrication method are also provided.

20 Claims, 5 Drawing Sheets

(56) References Cited

U.S. PATENT DOCUMENTS

| | | | | |
|---|---|---|---|---|
| 5,561,558 A * | 10/1996 | Shiono | ............... | G02B 5/1876 |
| | | | | 359/565 |
| 5,994,150 A * | 11/1999 | Challener | ............ | G01N 21/553 |
| | | | | 250/491.1 |
| 2002/0135780 A1* | 9/2002 | Budach | .............. | G01N 21/6452 |
| | | | | 356/521 |
| 2003/0231395 A1* | 12/2003 | Nakai | .................. | G02B 5/1876 |
| | | | | 359/558 |
| 2006/0262250 A1* | 11/2006 | Hobbs | .................... | G02B 5/201 |
| | | | | 349/96 |
| 2011/0049735 A1* | 3/2011 | Sakuma | ................ | G02B 6/124 |
| | | | | 264/1.24 |
| 2013/0023042 A1* | 1/2013 | Chang | ............ | G01N 33/54373 |
| | | | | 435/288.7 |
| 2017/0059405 A1* | 3/2017 | Huang | ................. | G01J 3/0218 |
| 2017/0319149 A1* | 11/2017 | Koehler | ................. | A61B 6/484 |
| 2019/0027265 A1* | 1/2019 | Dey | .................... | G01N 23/041 |

\* cited by examiner

BIOLOGICAL SIGNAL ANALYZING DEVICE, BIOLOGICAL SENSING APPARATUS, SENSING METHOD AND FABRICATION METHOD OF BIOLOGICAL SIGNAL ANALYZING DEVICE

TECHNICAL FIELD

The present invention is related to an optical device, sensing apparatus, sensing method and fabrication method, especially a biological signal analyzing device, biological sensing apparatus, sensing method and fabrication method of biological signal analyzing device.

BACKGROUND

As the technology develops, the application of optical detection devices for biological samples has always been one of the topics of research, wherein the guided-mode resonance of light is also a key topic in application technology. Since the guided-mode resonance can reflect specific wavelength which changes with the refractive index of the light transmitting medium, by making use of the characteristic, the concentration of the unknown biological sample can be calculated based on the refractive index. And if antibody is immobilized to the surface, the composition of the unknown biological sample can be further analyzed by this method.

However, in order to achieve high resolution optical wavelength analysis, the accuracy of the optical device used to generate the guided-mode resonance also needs to be improved. Optical device with high resolution is not only difficult to fabricate but also reduces the spectrum that can be detected per unit area. While providing a wide range of wavelength detection effects, it is inevitable to fabricate optical device with larger area accompanied by a wide range of sensing device, the production costs and difficulty will increase in all aspects. Therefore, how to enhance accuracy and increase measurement range of wavelength at the same time has been one of the crucial problems that need to be solved for optical detection devices applying guided-mode resonance.

SUMMARY

The present invention provides a biological signal analyzing device which can analyze the light of a sample and its condition.

The present invention provides a biological sensing device which can analyze a sample.

The present invention provides a sensing method for detecting the condition of the sample without labeling.

The present invention provides a fabricating method which fabricates the biological signal analyzing device that can analyze the condition of the sample.

The biological signal analyzing device of the present invention is used to generate a first detection image or a second detection image corresponding to the sample. The biological signal analyzing device includes light-incident surface, light-emitting surface and optical-resonance structures. The sample is suitable to be placed near the light-incident surface and receives a first light through the sample. The light-emitting surface is relative to the light-incident surface. The optical-resonance structures distribute on a filtering plane, extending along a first direction. The filtering plane is substantially parallel to the light-emitting surface, and the first direction is perpendicular to the normal of the filtering plane. The optical-resonance structures process the first light into a second light and a third light. The second light emits from the light-emitting surface and is suitable for forming a first detection image corresponding to the sample, the third light emits from the light-incident surface and is suitable for forming a second detection image corresponding to the sample. The thickness of optical-resonance structures changes along the first direction, or the width of the optical-resonance structures changes along the second direction which is perpendicular to the normal of filtering plane as well as the first direction.

In an example of the present invention, each of the aforementioned optical-resonance structure includes a first optical layer and a second optical layer. The first optical layer is disposed on the second optical layer along the normal of the filtering plane. The first optical layer is near the light-incident surface. The first optical layers of the optical-resonance structures are connected to each other, and the second optical layers of the optical-resonance structures are also connected to each other. The refractive index of the material of the first optical layer is higher than that of the second optical layer.

In an example of the present invention, the thickness of the first optical layers of the optical-resonance structures increases along the first direction.

In an example of the present invention, the width of the optical-resonance structures decreases along the second direction.

In an example of the present invention, the optical-resonance structures respectively correspond to different guided-mode resonance wavelengths by different thicknesses or widths.

In an example of the present invention, the difference between the guided-mode resonance wavelength of each optical-resonance structure on the first direction and the guided-mode resonance wavelength of the other adjacent optical-resonance structures is smaller than the difference between the guided-mode resonance wavelength of each optical-resonance structure on the second direction and the guided-mode resonance wavelength of the other adjacent optical-resonance structures.

The biological sensing apparatus of the present invention is used to measure a sample. The biological apparatus includes light source, sample loading surface, biological signal analyzing device and sensing device. The light source is for emitting the first light. The sample loading surface is suitable for loading samples. The biological analyzing device includes light-incident surface, light-emitting surface and optical-resonance structures. The sample loading surface is disposed near or formed on the light-incident surface. The optical-resonance structures distribute on the filtering plane, extending along the first direction. The filtering plane is substantially parallel to the light-emitting surface, and the first direction is perpendicular to the normal of the filtering plane. The optical-resonance structures are for processing the first light into a second light and a third light: the second light is emitted from the light-emitting surface, and the third light from the light-incident surface. The sensing apparatus includes a sensor, receiving the second light or the third light from the biological signal analyzing device. Upon receiving the second light, a first detection image corresponding to the sample is formed; and upon receiving the third light, a second detection image corresponding to the sample is formed. The thickness of the optical-resonance structures changes along the first direction, or the width of the optical-resonance structures changes along the second direction which is perpendicular to the normal of filtering plane as well as the first direction.

In an example of the present invention, each of the optical-resonance structures includes the first optical layer and the second optical layer. The first optical layer is disposed on the second optical layer along the normal of the filtering plane, and is near the light-incident surface. The first optical layers of the optical-resonance structures are connected each other, the second layers of the optical-resonance structures are also connected to each other, and the refractive index of the material of the first optical layer is higher than that of the second optical layer.

In an example of the present invention, the thickness of the first optical layers of the optical-resonance structures substantially increases along the first direction.

In an example of the present invention, the width of the optical-resonance structures decreases along the second direction.

In an example of the present invention, the optical-resonance structures respectively correspond to different guided-mode resonance wavelengths by different thicknesses or widths.

In an example of the present invention, the light source and the sensor substantially are disposed on the same side of the filtering plane, and the sensing surface of the sensor faces toward the light-incident surface to receive the third light from the biological signal analyzing device.

In an example of the present invention, the light source and the sensor are substantially disposed on opposite sides of the filtering plane, and the sensing surface of the sensor faces toward the light-emitting surface to receive the second light from the biological signal analyzing device.

In an example of the present invention, the difference between the guided-mode resonance wavelength of each optical-resonance structure on the first direction and the guided-mode resonance wavelength of the other adjacent optical-resonance structures is smaller than the difference between the guided-mode resonance wavelength of each optical-resonance structure on the second direction and the guided-mode resonance wavelength of the other adjacent optical-resonance structures.

A sensing method for biological sample is for sensing a sample, and the method includes:
providing a sample to the position near the light-incident surface of a biological signal analyzing device, wherein the biological signal analyzing device further includes optical-resonance structures;
irradiating the sample and the light-incident surface with a first light, allowing the biological signal analyzing device to receive the first light via the sample, and the optical-resonance structures processing the first light into a second light and a third light;
receiving the second light or the third light, using the second light to form a first detection image upon receiving the second light, and using the third light to form a second detection image upon receiving the third light;
obtaining the condition of the sample by the first detection image or the second detection image.

In an example of the present invention, the condition of the sample includes the concentration of the sample.

In an example of the present invention, the step of obtaining the condition of the sample includes:
when obtaining the first detection image, acquiring the first position where the center of the dark line of the first detection image is on a horizontal direction, wherein the dark line substantially extends along a vertical direction of the first detection direction; and
determining a first axis according to the first position, and acquiring a minimum position in the dark line of the first detection image along the first axis where the dark line has a minimum value, wherein the first axis is parallel to the vertical direction of the first detection image; converting the concentration of the sample according to the minimum position;
wherein the horizontal direction is substantially corresponding to the second direction of the biological signal analyzing device, and the vertical direction is substantially corresponding to the first direction of the biological signal analyzing device.

In an example of the present invention, the step of obtaining the condition of the sample includes:
when obtaining the second detection image, acquiring the second position where the center of the light line of the second detection image is on a horizontal direction, wherein the light line substantially extends along a vertical direction of the second detection image; and
determining a second axis according to the second position, and acquiring a maximum position in the light line of the second detection image along the second axis where the light line has a maximum value, wherein the second axis is parallel to the vertical direction of the second detection image;
converting the concentration of the sample according to the maximum position;
wherein the horizontal direction substantially corresponds to the second direction of the biological signal analyzing device, and the vertical direction substantially corresponds to the first direction of the biological signal analyzing device.

A fabricating method for the biological signal analyzing device includes:
providing a substrate;
forming a second optical layer on the substrate;
forming micro-structures on the second optical layer by lamination, imprinting or etching; and forming a first optical layer on the second optical layer to create optical-resonance structures, wherein the refractive index of the material of the first optical layer is higher than that of the second optical layer.

In an example of the present invention, the micro-structures extend along the first direction, the thickness of the micro-structures increases along the first direction, the width of the micro-structures decreases along the second direction, and the second direction is perpendicular to the first direction.

In an example of the present invention, the first optical layer is formed on the second optical layer by means of sputtering, and the normal of the loading surface of the substrate is not parallel to the normal of the surface of the target when sputtering, the first optical layer is formed on the loading surface.

As seen from the above, the present invention proposes a biological signal analyzing device and the fabrication method thereof that can generate the second light or the third light corresponding to the sample, allowing the processed second light or the third light to carry the conditions of the sample. The biological sensing apparatus and the sensing method proposed by the present invention are capable of analyzing the wavelength of the first light with a wider wavelength rage and a higher accuracy by the aforementioned biological signal analyzing device.

EMBODIMENT

The biological signal analyzing device proposed by the present invention can be matched with the sensor of, for instance, charged-coupled device (CCD) or CMOS active pixel sensor as well as imaging materials such as negative and etc., so as to form detection image by the light emitting from the biological signal analyzing device, but the present invention is not limited to the sensor's types.

It should be understandable that, despite the term "the first", "the second" and etc. in the text can be used to describe any kind of light, device, area or parts, the lights, devices, area or parts should not be limited by these terms. These terms are used merely to separate a light, device, area or part from another light, device, area or part.

Figure 1A:
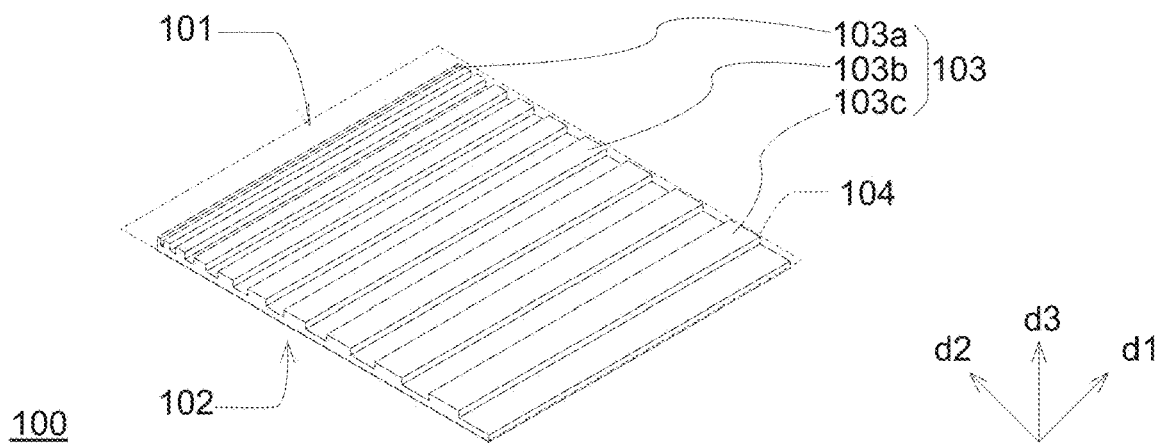
FIG. 1A to FIG. 1C are the schematic views of the biological signal analyzing device of the first to the third example of the present invention.
Figure 1B:
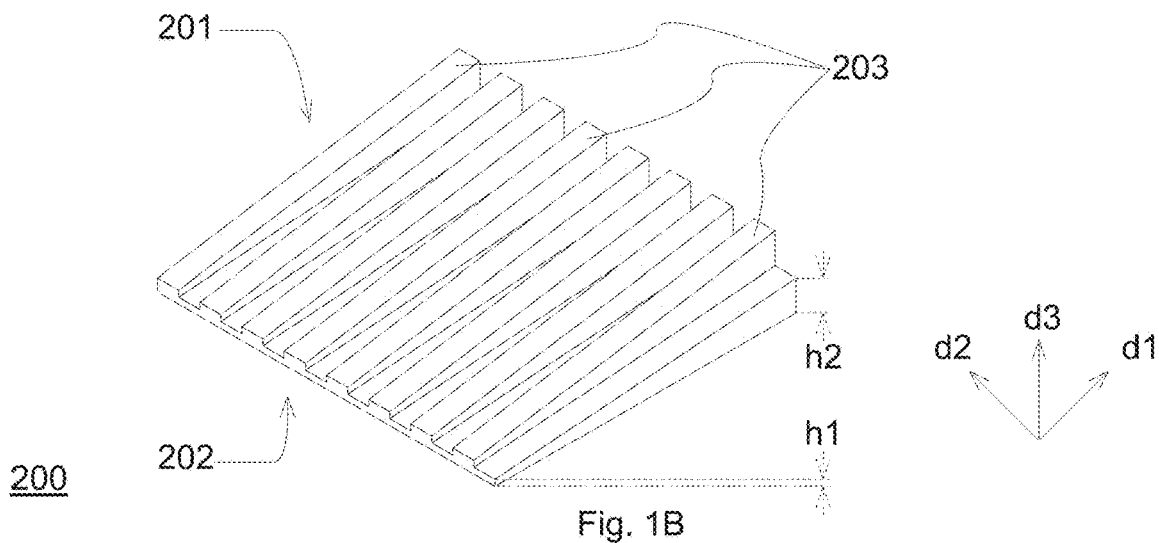
Figure 1C:
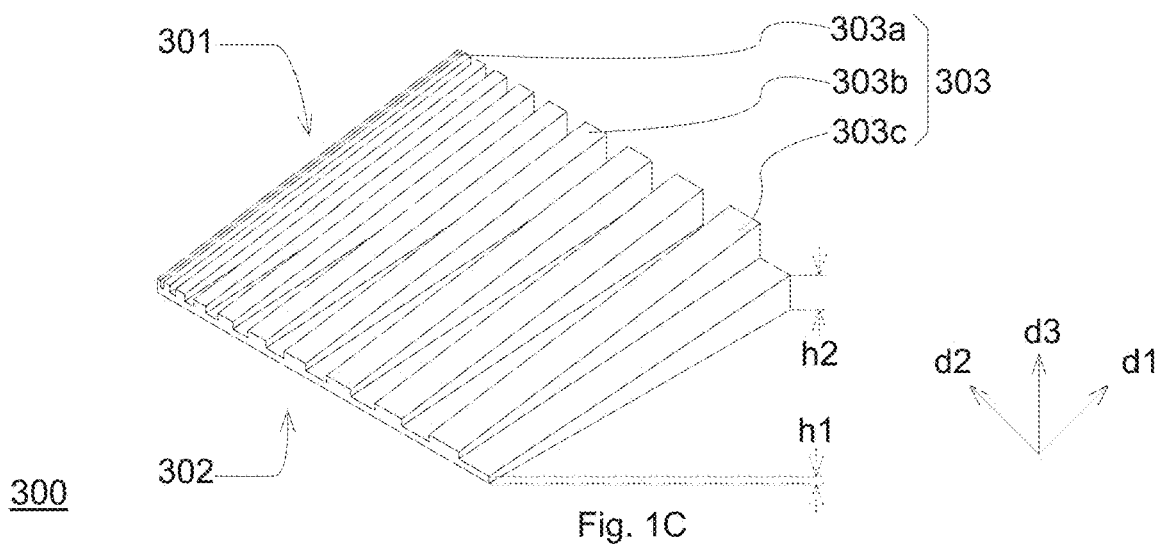

FIG. 1A to FIG. 1C are the perspective view of the biological signal analyzing device of the first to the third example of the present invention, this is mainly for illustrating the distribution of the optical-resonance structures on the optical signal analyzing device in the example of the present invention, so the detailed layered structure is omitted, but it is not intended to limit the invention. Please refer to FIG. 1A, in the first example of the present invention, the biological signal analyzing device 100 includes light-incident surface 101 and light-emitting surface 102, and optical-resonance structures 103 distributing along the filtering plane 104. The filtering plane 104 is a virtual plane locating between the light-incident surface 101 and the light-emitting surface 102. After receiving a first light from the light-incident surface 101, the biological signal analyzing device 100 of the example substantially forms a second light and a third light that can respectively generates detection image via the process of the optical-resonance structures 103 on the filtering plane 104, wherein the second light is emitted from the light-emitting surface 102, and the third light from the light-incident surface 101.

In the first example, the distribution density of the optical-resonance structures 103 increases gradually along a direction. Please refer to FIG. 1A, the optical-resonance structures 103 of the example extend respectively along the first direction d1 and arrange along the second direction d2. In the second direction d2, the distribution density of the optical-resonance structures increases and width decreases, that is, in the unit area projected on the filtering plane 104, the projected area of the optical-resonance structure 103c is bigger than that of the optical-resonance structure 103b, and the projected area of the optical-resonance structure 103b is bigger than that of the optical-resonance structure 103a.

What needs to be specified is that the optical-resonance structures proposed by the present invention are not limited to protruding structures as the optical-resonance structures 103 aforementioned, in other examples, the materials having different refractive index may be mutually connected to each other, and the width thereof may be adjusted to achieve the effects of the present invention.

Please refer back to FIG. 1A. In other words, in the first example of the present invention, in the second direction d2, the optical-resonance structure 103c of the example is larger than the optical-resonance structure 103b in terms of period or distribution period, and the optical-resonance structure 103b is larger than the optical-resonance structure 103a. The optical-resonance structures 103 are formed in the biological signal analyzing device 100 in the aforementioned manner, allowing the biological signal analyzing device 100 to generate different second light and third light corresponding to light of different wavelengths, thereby generating different detection images.

To be specific, the biological signal analyzing device 100 of the first example of the present invention is, for instance, a gradient grating period guided-mode resonance (GGP-DMR) device. The optical-resonance structures 103 are formed on a substrate (not marked) and is suitable for the incident light to generate guided-mode resonance (GMR), allowing the biological signal analyzing device 100 to form, for instance, a band-stop filter, so that a part of the incident light of particular wavelength can be reflected by the light-incident surface 101 and the rest be transmitted to the light-emitting surface 102. The aforementioned particular wavelength that generates resonance will also be changed because of the refractive index of the sample loaded on the light-incident surface 101 of the biological signal analyzing device 100, so the detection image provided by the biological signal analyzing device 100 can also help obtain the conditions such as the concentration of the sample.

On the other hand, by changing the period of the optical-resonance structures 103, the resonance wavelength of each optical resonant structure 103 can also be changed correspondingly, so that the biological signal analyzing device 100 can generate different detection images corresponding to light of different wavelengths.

The biological signal analyzing device of the present invention is not limited by the aforementioned biological signal analyzing device 100, the incident first light can further be processed into the second light and the third light by the thickness variation of the optical-resonance structure. Please refer to FIG. 1B, in the second example of the present invention, the biological signal analyzing device 200 includes light-incident surface 201, light-emitting surface 202, and optical-resonance structures 203 extending along the first direction d1 and distributing along the second direction d2. The biological signal analyzing device 200 of the example is essentially similar to the aforementioned biological signal analyzing device 100, except that the distribution density and width of the optical-resonance structures 203 along the second direction d2 are substantially the same, but the thickness of each optical-resonance structure 203 gradually increases along the first direction d1.

Please refer to FIG. 1B, in the first direction d1, the thickness of one end of the optical-resonance structures 203 is h1, and the thickness of the opposite end is h2, wherein the thickness is the height of the optical-resonance structures 203 in the third direction d3. The optical-resonance structures 203 extend along the first direction d1, and thickness of the optical-resonance structures 203 increases along the first direction d1 as well, allowing the biological signal analyzing device 200 to generate different second light and third light corresponding to the first light of different wavelengths, thereby generating different detection images.

To be precise, the biological signal analyzing device 200 in the second example of the present invention is a gradient waveguide thickness guided-mode resonance (GWT-GMR) device. In the first direction d1, each optical-resonance structure 203 corresponds to different resonance wavelength due to the differences of thickness, thus the biological signal analyzing device 200 can generate different detection images corresponding to the first light of different wavelengths. The aforementioned particular wavelength that generates resonance will also be changed because of the refractive index of the sample loaded on the light-incident surface 201 of the biological signal analyzing device 200, so the detection image provided by the biological signal analyzing device 200 can also help obtain the conditions such as the concentration of the sample.

The optical-resonance structures of the biological signal analyzing device in the example of the present invention can also have width and thickness variations at the same time. Please refer to FIG. 1C, in the third example of the present invention, the biological signal analyzing device 300 includes light-incident surface 301 and light-emitting surface 302 and further includes optical-resonance structures 303. The optical-resonance structures 303 extend along the first direction d1 and arrange along the second direction d2, and the distribution density of the optical-resonance structures 303 increases along the second direction d2. In other words, the width of the optical-resonance structure 303 decreases along the second direction d2, wherein the period of the optical-resonance structure 303a is smaller than that of the optical-resonance structure 303b, and the period of the optical-resonance structure 303b is smaller than that of the optical-resonance structure 303c.

Moreover, the thickness of each optical-resonance structure 303 of the example also changes along the first direction d1. Please refer to FIG. 1C, taking the optical-resonance structure 303c as an instance, the thickness of the part of the structure on one end in the first direction d1 is h1, whereas the thickness of the part of the structure on the other end in the first direction d1 increases to h2, wherein the thickness is the height of the optical-resonance structures 303 in the third direction d3. By simultaneously changing the thickness and period of the optical-resonance structures 303, the biological signal analyzing device 300 can generate different detection images corresponding to the first light of different wavelengths.

To be specific, the biological signal analyzing device 300 of the second example of the present invention is a two dimensional gradient guided-mode resonance (TDG-GMR) device. The optical-resonance structures 303 are suitable for the incident first light to generate guided-mode resonance, and while each of the optical-resonance structures 303 extends along the first direction, the thickness changes as well. In the second direction d2, the width of the optical-resonance structures 303 decreases toward a direction, that is, the optical-resonance structures 303 are distributed in a periodically increasing manner.

Preferably, the thickness variation of the optical-resonance structures 303 of the example increases linearly, each area can continuously correspond to different resonance wavelengths as the thickness changes, allowing the biological signal analyzing device 300 to generate different detection images corresponding to the wavelength with minor variation. In other words, by changing the width variation of the optical-resonance structures 303 in the second direction d2, a larger range of resonance wavelength can be corresponded to, and thus the incident light in a large spectrum can be measured. And by changing the thickness variation of the optical-resonance structures 303 in the first direction d1, it is possible to analyze the different signals generated from the corresponding wavelength with minor differences, so as to provide measurement results with higher accuracy.

On the other hand, the periodical variation of the optical-resonance structures 303 of the example can widen the detectable spectrum for the biological signal analyzing device 300 without forming a length that is too long in the first direction d1. In other words, the biological signal analyzing device 300 of the example can widen the range as well as reduce the limit of the detection with the help of the optical-resonance structures 303.

The following will make use of the aforementioned biological signal analyzing device 300 to elaborate the biological sensing apparatus proposed by the example below. However, the biological signal analyzing device 300 and the biological sensing apparatus proposed by the present invention are not limited to this, person having ordinary skill in the art can adjust or replace them with any of the biological signal analyzing devices mentioned above if necessary.

Figure 2A:
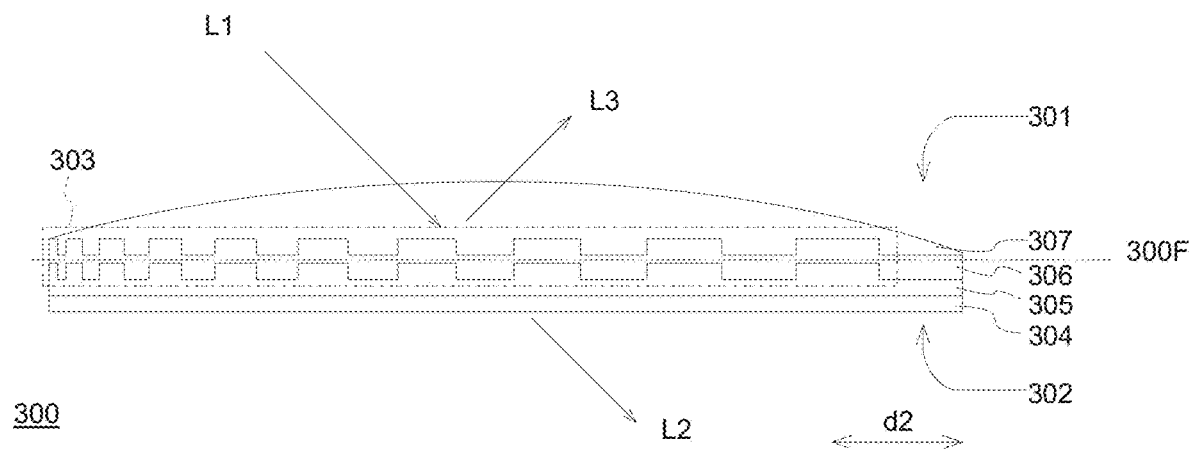
FIG. 2A is the section view of the biological signal analyzing device of the third example.

Please refer to the section view of the biological signal analyzing device of the third example illustrated in FIG. 2A, wherein the section line in FIG. 2A is, for instance, following the aforementioned second direction d2. In the example, the biological signal analyzing device 300 includes the first optical layer 306 and the second optical layer 305. The second optical layer is, for instance, formed on the substrate 304 by lamination, imprinting or etching, the first optical layer 306 is formed on the second optical layer 305, and the first optical layer 306 is substantially disposed on the second optical layer 305 along the normal of the filtering plane 300F. The first optical layer 306 is near the light-incident surface 301, and the second optical layer 305 near the light-emitting surface 302.

In the example, the refractive index of the material of the first optical layer 306 is higher than that of the second optical layer 305, and by forming the shape of the optical-resonance structures 303, the incident first light L1 via the light-incident surface 301 can generate resonance. To be explicit, the sample loading surface of the example is substantially formed on the first optical layer 306, and the sample 307 is disposed on the first optical layer 306. The first light L1 is transmitted to the light-incident surface 301 through the sample 307; to be more specific, the first light L1 is transmitted to the optical-resonance structures 303 through the interface between the sample 307 and the first optical layer 306. The first light L1 can be processed into the second light L2 and the third light L3 by the resonance of the optical-resonance structures 303, wherein the second light L2 is emitted from the light-emitting surface 302, and the third light L3 from the light-incident surface 301. The wavelength of the third light L3 can be, for instance, the particular resonance wavelength of the optical-resonance structures 303 of the example, and the wavelength of the second light L2 falls within other ranges.

For instance, the material of the second optical layer 305 of the example is, for instance, light curing adhesive; the material of the substrate is, for instance, polyethylene terephthalate (PET); the material of the first optical layer 306 is, for instance, TiO2. To be explicit, the second optical layer 305 of the example can be made into a master mold by using silicon as material and by means of the e-beam lithography system in micro/nano fabrication and etching, the coating is, for instance, the optical curing adhesive of Norland Optical Adhesive, Norland Products Inc., curing on the substrate 304 to become the second optical layer 305.

Figure 2B:
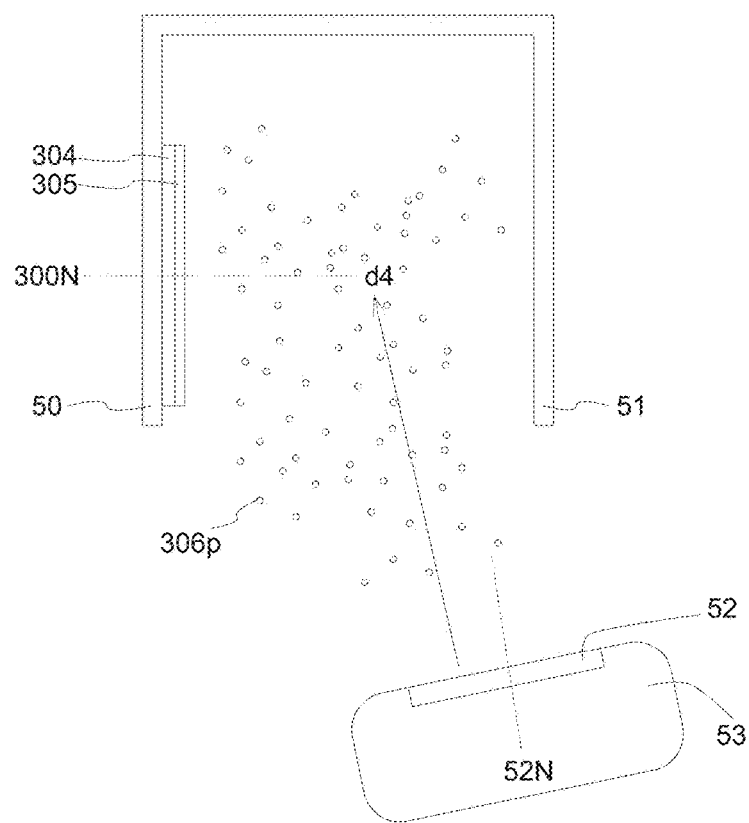
FIG. 2B is the fabrication schematic view of the biological signal analyzing device of the third example.

The first optical layer 306 is fabricated by sputter, and the first optical layer 306 acts as a waveguide layer on the second optical layer 305. Please refer to the fabrication schematic view of the biological signal analyzing device of the third example illustrated in FIG. 2B. When sputtering the first optical layer 306 of the example, the normal of the filtering plane (namely the normal 300N of the loading surface of the substrate 304) is substantially not parallel to the surface normal 52N of the target 52. Specifically, the target 52 on the rack 53 is facing the substrate 304 and the second optical layer 305 along the direction d4, and one end of the second optical layer 305 is closer to the target 52, receiving more TiO2 306p, whereas the other end is farther from the target 52, receiving less TiO2 306p. By the sputtering, the aforementioned thickness of the first optical layer 306 can be formed in a gradually decreased manner. Furthermore, the substrate 304 and the second optical layer 305 are disposed on the upright substrate 50, and the baffle 51 can prevent the rebound of TiO2 306p from further affecting the thickness of the formed first optical layer, and thus the first optical layer having an increasing thickness can be formed.

The following will further elaborate on the biological sensing apparatus including the aforementioned biological signal analyzing device 300. The biological sensing apparatus proposed by the present invention can measure a sample in a penetration mode or a reflection mode.

Penetration Mode

Figure 3A:
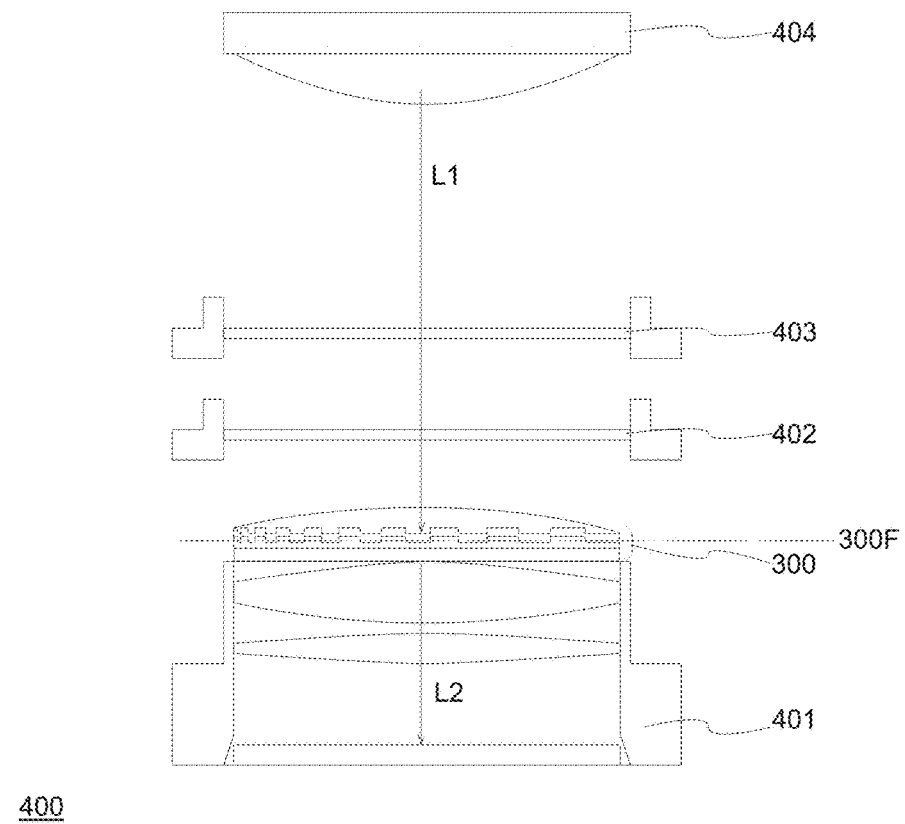
FIG. 3A is the schematic view of the biological sensing apparatus in an example of the present invention.

Please refer to the schematic view of the biological sensing apparatus 400 of an example of the present invention illustrated in FIG. 3A. The biological sensing apparatus 400 includes light source 404, filter 403, polarizer 402, the aforementioned biological signal analyzing device 300 and sensor 401. To see from the filtering plane 300F of the biological signal analyzing device 300, the light source 404, filter 403 and polarizer 402 of the example are disposed on the same side, and the sensor is disposed on the opposite side.

The light source 404 is, for instance, an narrowband laser light source for emitting the first light L1 of a single wavelength, allowing the second light L2 to form corresponding detection image according to the sample. That is to say, by making use of the difference of the refractive index of the sample and the effective index of the biological signal analyzing device 300, the light resonates in partial optical-resonance structures, thus the second light L2 can form at least a dark line in the first detection image, and the position of the dark line changes correspondingly to the refractive index of the sample.

The filter 403 is for controlling the intensity of the first light L1, and the polarizer 402 is for adjusting the polarization direction of the first light L1, allowing the first light L1 to resonate within the biological signal analyzing device 300. The sensor 401 can be CCD or CMOS, but the present invention is not limited to these. The biological signal analyzing device 300 of the example is disposed on the sensing surface of the sensor 401, thus the biological sensing apparatus 400 can obtain the conditions of the sample by sensing the second light L2 from the biological signal analyzing device 300. In other words, the distribution range of the biological signal analyzing device 300 covers the sensing area of the sensor 401, allowing the light falling within the range of non-particular wavelength after the guided-mode resonance to be formed into the second light L2 which can be received by the sensor 401 and formed into the first detection image.

Reflection Mode

Figure 3B:
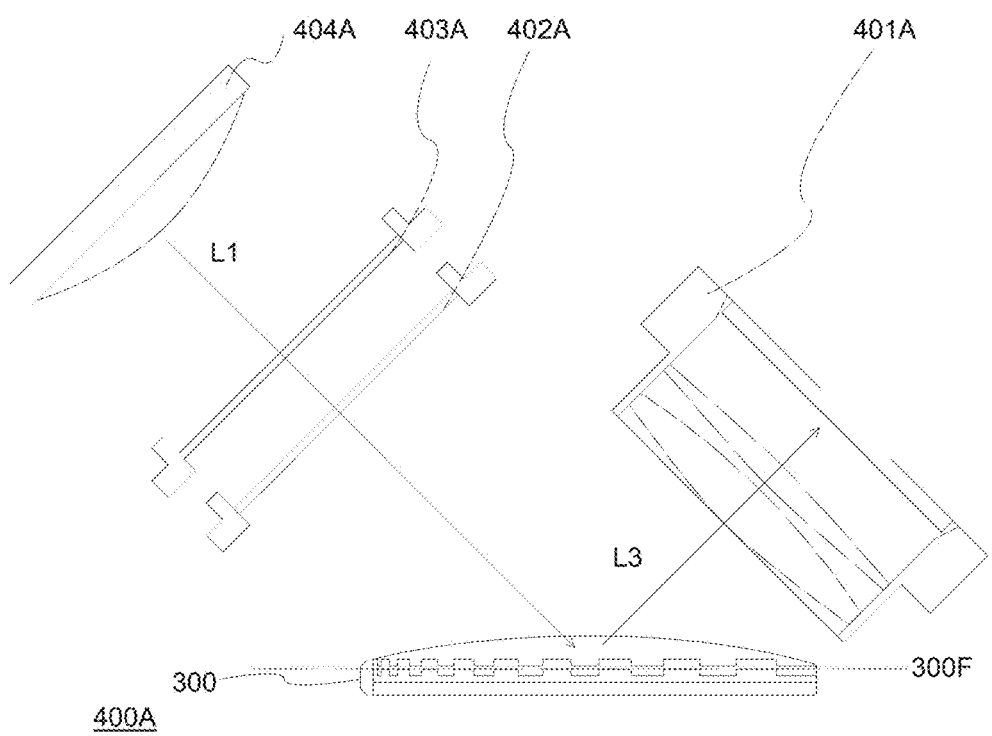
FIG. 3B is the schematic view of the biological sensing apparatus in another example of the present invention.

Please refer to the schematic view of the biological sensing apparatus 400A of an example of the present invention illustrated in FIG. 3B. The biological sensing apparatus 400A includes light source 404A, filter 403A, polarizer 402A, the aforementioned biological signal analyzing device 300 and sensor 401A. To see from the filtering surface 300F of the biological signal analyzing device 300, the light source 404A, filter 403A, polarizer 402A and the sensor 401A are disposed on the same side.

In the example, the sensor 401A is suitable for receiving the third light L3 emitting from the light-incident surface of the biological signal analyzing device 300, namely, the light of particular wavelength that cannot penetrate through the biological signal analyzing device 300 due to guided-mode resonance. The third light L3 is formed into the second detection image after being received by the sensor 401A, wherein the second detection image includes at least a light line, that is, the image formed by the light which is reflected due to guided-mode resonance.

Figure 4A:
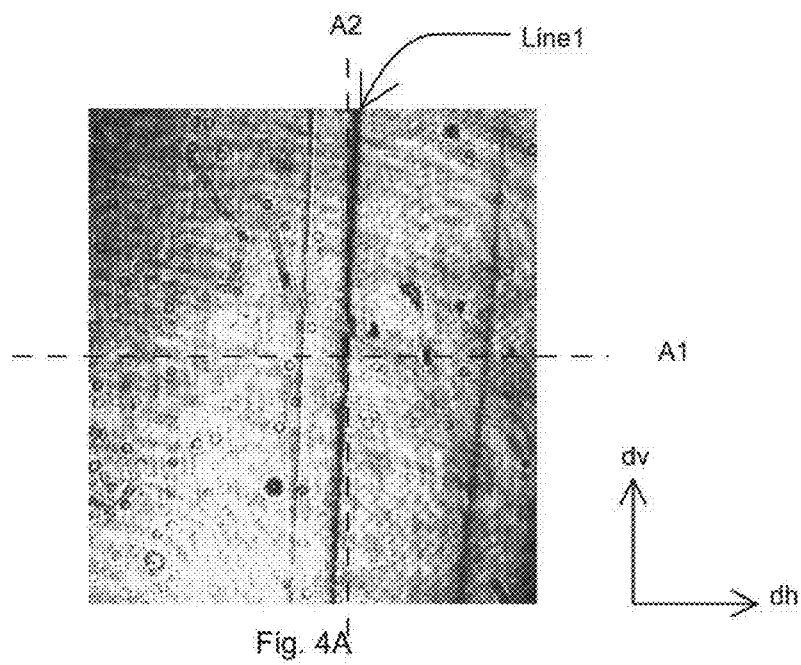
FIG. 4A is the schematic view of the first detection image in an example of the present invention.

The following will further elaborate on the sensing method proposed by the present invention. Taking the aforementioned biological sensing apparatus 400 as an instance, FIG. 4A is the schematic view of the first detection image in an example of the present invention, wherein a dark line Line1 is included. The sample is, for instance, the 23.5% sugar solution, and in the sensing method of the example, the distribution of signal intensity in the horizontal direction dh of the detection image needs to be located first in order to obtain the center position of the dark line Line1. The center position here is, for instance, the position of the lowest signal intensity corresponded to the dark line Line1.

Figure 4B:
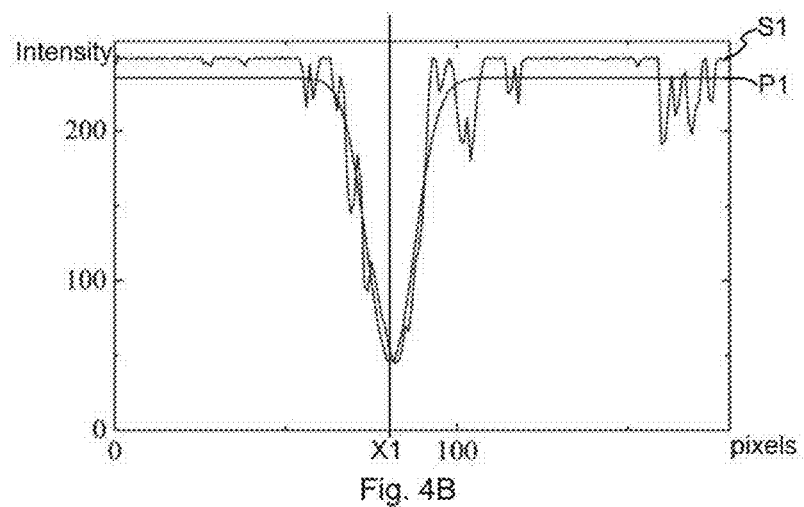
FIG. 4B is the signal schematic view and regression curve along the axis A1 in FIG. 4A.

Please refer to FIG. 4B, the diagram of the signal intensity distribution illustrated according to the axis A1 in FIG. 4A: the horizontal axis is the pixel position and the vertical axis is the intensity (unit A.U.). The sensing method of the example is to locate the center position as the first position X1 according to the diagram of the signal intensity distribution, and the first position X1 here, for instance, is the position of the lowest signal intensity. Specifically, the sensing method of the example is to acquire the regression curve P1 of the signal S1, and then obtain the first position X1 according to the regression curve P1. The axis A1 here, for instance, is the center position in the vertical direction dv of the first detection image, but the present invention is not limited to this. In other examples, the position of the axis A1 in the vertical direction dv can further be adjusted as needed.

Figure 4C:
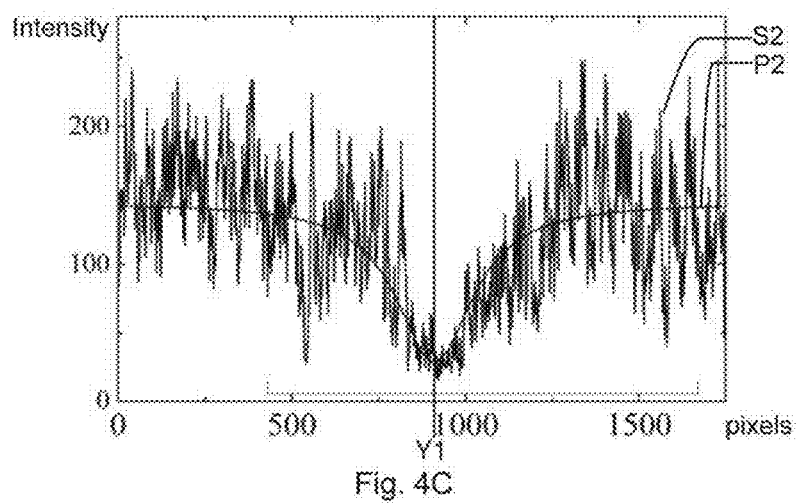
FIG. 4C is the signal schematic view and regression curve along the axis A2 in FIG. 4A.

Please refer back to FIG. 4A, after the center position X1 is determined, the axis A2 can also be determined according to the pixel position of the center position X1, and then the diagram of the signal intensity distribution in the vertical direction (FIG. 4C) can be obtained according to the axis A2. Here, for instance, taking the axis A2 that passes through the center position X1 as an example, in other examples of the present invention, it can be further divided into areas along the direction dh to determine an axis respectively (such as determining the axis of each area by the center position along the direction dh). Please refer to FIG. 4C, the regression curve P2 is obtained according to the signal S2, and the minimum position Y1 of the regression curve P2 is also obtained.

Figure 5A:
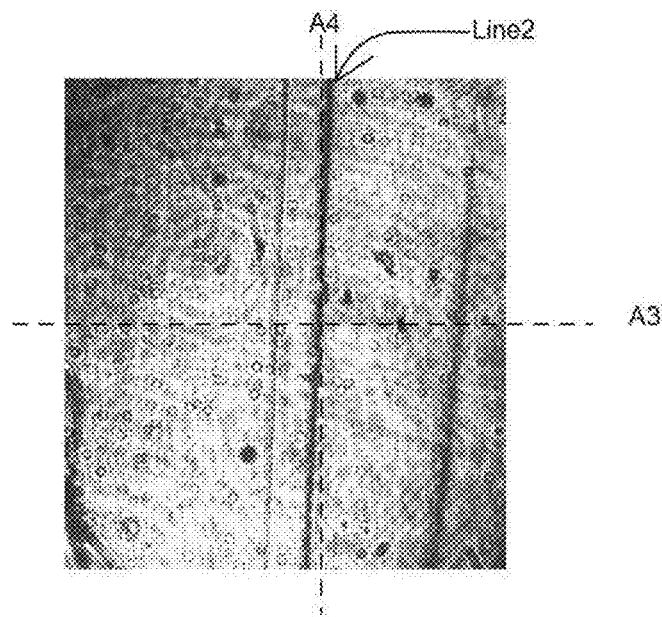
FIG. 5A is the schematic view of another first detection image in the example of the present invention.
Figure 5B:
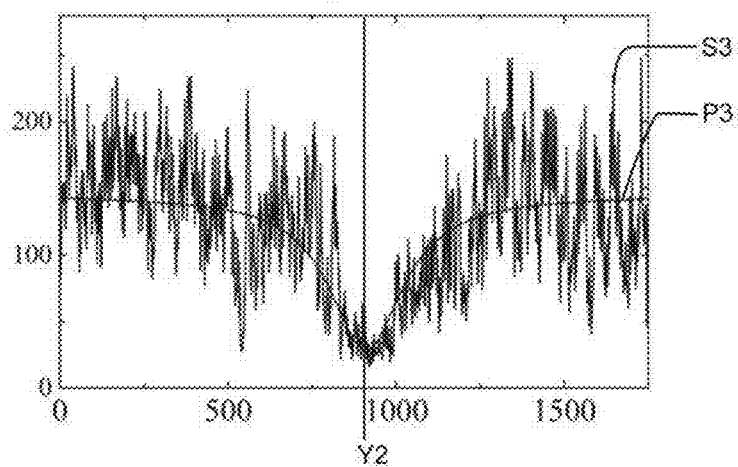
FIG. 5B is the signal schematic view and regression curve along the axis A4 in FIG. 5A.
Figure 5C:
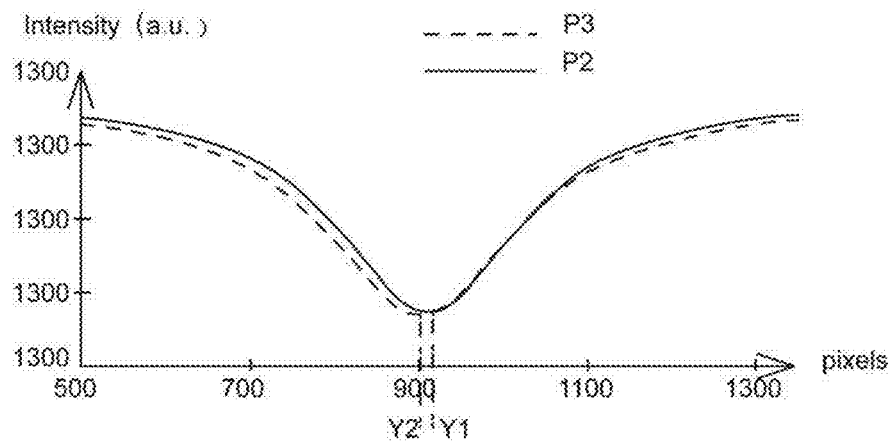
FIG. 5C is the comparison chart of the regression curves in FIG. 4C and FIG. 5B.

In a sample of another concentration, the sensing method of the example again acquires another first detection image as illustrated in FIG. 5A, wherein, by using the above steps, the first position is obtained according to the axis A3, and the axis A4 is determined in order to obtain the diagram of the signal intensity distribution as shown in FIG. 5B, wherein the signal curve S3 determines the regression curve P3 and acquires the minimum position Y2. Please note that the two samples with similar concentrations are taken as an example, that is, the dark lines in the detection image are similar or identical in the direction dh. For instance, the dark lines of both detection images substantially fall within the same image area or pixel area, so the relative position of the aforementioned axis A3 in the detection image is the same as or close to the relative position of the aforementioned axis A1 in the detection image. In other words, the sensing method of the example is divided into different image areas or pixel areas in the dh direction, and different areas correspond to different dv direction axes, so the sensing method can further analyze the corresponding concentration of the signals according to the axis. The detailed analysis method is elaborated as follows Please refer to FIG. 5C, which compares the regression curve P2 in FIG. 4C and the regression curve P3 in FIG. 5B, both of the lowest position Y1 and Y2 shift to correspond to different sample concentrations. Therefore, by the calibration method mentioned above, the corresponding sample concentration can be determined by the aforementioned minimum position, and thus other samples with unknown concentrations can also be measured.

The conditions of the above samples are exemplified by the concentration, but the present invention is not limited to this. Other conditions of the sample that change the refractive index can also be measured in other examples. On the other hand, the sensing method above is elaborated by the biological sensing apparatus with penetration mode, in other examples, if to elaborate by the biological sensing apparatus with reflection mode proposed by the present invention, then the dark line of the aforementioned detection image should be light line, and the corresponding minimum should be a maximum. Person having ordinary skill in the art should be able to apply correspondingly to the biological sensing apparatus with reflection mode as needed based on the content above, so no detail will be described here.

In conclusion, the biological signal analyzing device and the fabricating method thereof proposed by the present invention, including the biological sensing apparatus and sensing method of the aforementioned biological signal analyzing device, can provide an optical sensing function of a wide range and high accuracy, and samples can be measured without marking.

What is claimed is:

1. A biological signal analyzing device which is configured to generate a first detection image or a second detection image corresponding to a sample, and the biological signal analyzing device including:
    a light-incident surface, of which the sample is suitable for being placed nearby, collecting a first light through the sample;
    a light-emitting surface, relative to the light-incident surface; and
    a plurality of optical-resonance structures, distributing on a filtering plane and extending along a first direction, wherein the filtering plane is substantially parallel to the light-emitting surface, and the first direction is perpendicular to the normal of filtering plane;
    wherein the optical-resonance structures process the first light into a second light and a third light, the second light is emitted from the light-emitting surface and is adapted to form a first detection image of the sample, and the third light is emitted from the light-incident surface and is adapted to form a second detection image of the sample;
    and in the biological signal analyzing device, thickness of each optical-resonance structure increases along first direction, and the width of the optical-resonance structures changes along second direction which is perpendicular to the normal of filtering plane as well as the first direction.

2. The biological signal analyzing device of claim 1, wherein each of the optical-resonance structures includes:
    a first optical layer; and
    a second optical layer, wherein the first optical layer is disposed on the second optical layer along the normal of the filter plane, near the light-incident surface;
    wherein the first optical layers of the optical-resonance structures are connected to each other, the second optical layers of the optical-resonance structures are also connected to each other, and the refractive index of the material of the first optical layer is higher than that of the second optical layer.

3. The biological signal analyzing device of claim 2, wherein the thickness of the first optical layers of the optical-resonance structures substantially increases along the first direction.

4. The biological signal analyzing device of claim 2, wherein the width of the optical-resonance structures decreases along the second direction.

5. The biological signal analyzing device of claim 1, wherein the optical-resonance structures respectively correspond to different guided-mode resonance wavelengths by different thicknesses or widths.

6. The biological signal analyzing device of claim 5, wherein the difference between the guided-mode resonance wavelength of each optical-resonance structure on the first direction and the guided-mode resonance wavelength of the other adjacent optical-resonance structures is smaller than the difference between the guided-mode resonance wavelength of each optical-resonance structure on the second direction and the guided-mode resonance wavelength of the other adjacent optical-resonance structures.

7. A biological sensing apparatus for measuring a sample including:
    a light source, being configured to emit a first light;
    a sample loading surface, being adapted to load the sample;
    a biological signal analyzing device, including:
        a light-incident surface, of which the sample loading surface is disposed nearby or formed on;
        a light-emitting surface, relative to the light-incident surface; and
        light-resonance structures, being distributed on a filtering plane, extending along the first direction,
    wherein the filtering plane is substantially parallel to the light-emitting surface, the first direction is perpendicular to the normal of filtering plane, the light-resonance structures process the first light into a second light emitting from the light-emitting surface and a third light emitting from the light-incident surface; and a sensor, including a sensing surface for receiving the second light or the third light from the biological signal analyzing device, forming a first detection image corresponding to the sample upon receiving the second light and forming a second detection image corresponding to the sample upon receiving the third light;

wherein in the biological signal analyzing device, the thickness of the each optical-resonance structure increases along the first direction, and the width of the optical-resonance structures changes along the second direction which is perpendicular to the normal of filtering plane as well as the first direction.

8. The biological sensing apparatus of claim 7, wherein each optical-resonance structure includes:

a first optical layer; and a second optical layer, the first optical layer being disposed on the second optical layer along the normal of the filtering plane, near the light-incident surface;

wherein the first optical layers of the optical-resonance structures are connected to each other, the second optical layer of the optical-resonance structures are also connected to each other, and the refractive index of the material of the first optical layer is higher than that of the second optical layer.

9. The biological sensing apparatus of claim 8, wherein the thickness of the first optical layers of the optical-resonance structures substantially increases along the first direction.

10. The biological sensing apparatus of claim 8, wherein the width of the optical-resonance structures decreases along the second direction.

11. The biological sensing apparatus of claim 7, wherein the optical-resonance structures respectively correspond to different guided-mode resonance wavelengths by different thicknesses or widths.

12. The biological sensing apparatus of claim 7, wherein the light source and the sensor are substantially disposed on the same side of the filtering plane, and the sensing surface of the sensor faces toward the light-incident surface to receive the third light from the biological signal analyzing device.

13. The biological sensing apparatus of claim 7, wherein the light source and the sensor are substantially disposed on opposite sides of the filtering plane, and the sensing surface of the sensor faces toward the light-emitting surface to receive the second light from the biological signal analyzing device.

14. The biological sensing apparatus of claim 6, wherein the difference between the guided-mode resonance wavelength of each optical-resonance structure on the first direction and the guided-mode resonance wavelength of the other adjacent optical-resonance structures is smaller than the difference between the guided-mode resonance wavelength of each optical-resonance structure on the second direction and the guided-mode resonance wavelength of the other adjacent optical-resonance structures.

15. A sensing method for biological sample used to sense a sample, the method including:

providing the sample to position near the light-incident surface of a biological signal analyzing device, wherein the biological signal analyzing device further includes optical-resonance structures;

irradiating the sample and the light-incident surface with a first light, allowing the biological signal analyzing device to receive the first light via the sample, and the optical-resonance structures processing the first light into a second light and a third light;

receiving the second light or the third light, using the second light to form a first detection image upon receiving the second light, and using the third light to form a second detection image upon receiving the third light; and obtaining the condition of the sample by the first detection image or the second detection image, wherein the optical-resonance structures extend along a first direction, the thickness of the optical-resonance structures increases along the first direction, the width of the optical-resonance structures decreases along a second direction, and the second direction is perpendicular to the first direction.

16. The sensing method of claim 15, wherein the condition of the sample includes the concentration of the sample.

17. The sensing method of claim 15, wherein the step of obtaining the condition of the sample includes:

when obtaining the first detection image, acquiring first position where the center of the dark line of the first detection image is on a horizontal direction, wherein the dark line substantially extends along a vertical direction of the first detection direction; and determining a first axis according to the first position, and acquiring a minimum position in the dark line of the first detection image along the first axis where the dark line has a minimum value, wherein the first axis is parallel to the vertical direction of the first detection image;

converting the concentration of the sample according to the minimum position;

wherein the horizontal direction substantially corresponds to the second direction of the biological signal analyzing device, and the vertical direction substantially corresponds to the first direction of the biological signal analyzing device.

18. The sensing method of claim 15, wherein the step of obtaining the condition of the sample includes:

when obtaining the second detection image, acquiring a second position where the center of the light line of the second detection image is on a horizontal direction, wherein the light line substantially extends along a vertical direction of the second detection image; and determining a second axis according to the second position, and acquiring a maximum position in the light line of the second detection image along the second axis where the light line has a maximum value, wherein the second axis is parallel to the vertical direction of the second detection image;

converting the concentration of the sample according to the maximum position;

wherein the vertical direction substantially corresponds to the first direction of the biological signal analyzing device, and the horizontal direction substantially corresponds to the second direction of the biological signal analyzing device.

19. A fabricating method of the biological signal analyzing device including:

providing a substrate;

forming a second optical layer on the substrate;

forming a plurality of micro-structures on the second optical layer by lamination, imprinting or etching; and forming a first optical layer on the second optical layer to create optical-resonance structures, wherein the refractive index of the material of the first optical layer is higher than that of the second optical layer, wherein the micro-structures extend along a first direction, the thickness of the micro-structures increases along the first direction, the width of the micro-structures decreases along a second direction, and the second direction is perpendicular to the first direction.

20. The fabricating method of claim 19, wherein the first optical layer is formed on the second optical layer by means of sputtering, and the normal of the loading surface of the substrate is not parallel to the normal of the surface of the target when sputtering, the first optical layer is formed on the loading surface.

\* \* \* \* \*